United States Patent
Cotticelli et al.

(10) Patent No.: US 7,482,476 B2
(45) Date of Patent: Jan. 27, 2009

(54) PROCESS FOR THE PREPARATION OF 5-CYANOPHTHALIDE STARTING FROM 5-CARBOXYPHTHALIDE

(75) Inventors: Giovanni Cotticelli, Milan (IT); Raul Salvetti, Malonno (IT); Marco Zappa, Abbiategrasso (IT)

(73) Assignee: Adorkem Technology SpA, S. Costa Volpino (Bergamo) (IT)

( * ) Notice: Subject to any disclaimer, the term of this patent is extended or adjusted under 35 U.S.C. 154(b) by 0 days.

(21) Appl. No.: 11/581,133

(22) Filed: Oct. 13, 2006

(65) Prior Publication Data

US 2007/0117991 A1 May 24, 2007

(30) Foreign Application Priority Data

Oct. 14, 2005 (EP) .................................. 05425720

(51) Int. Cl.
*C07D 307/00* (2006.01)
(52) U.S. Cl. ..................................................... 549/467
(58) Field of Classification Search ................... 549/467
See application file for complete search history.

(56) References Cited

U.S. PATENT DOCUMENTS 6,441,201 B1 * 8/2002 Weber ........................ 549/468

FOREIGN PATENT DOCUMENTS

WO    WO 00/39112       7/2000

OTHER PUBLICATIONS

Liguori et al., *Synthesis*, 2:168 (1987).

* cited by examiner

*Primary Examiner*—D. Margaret Seaman
*Assistant Examiner*—Nizal S Chandrakumar
(74) *Attorney, Agent, or Firm*—Perkins Coie LLP

(57) ABSTRACT

A new process is described for obtaining 5-cyanophthalide, which is an intermediate used for the synthesis of citalopram and its active enantiomer S(+) citalopram, both of which are known active ingredients commonly used for treating depression. The process involves starting from 5-carboxyphthalide which is converted into the corresponding acylochloride. The latter is reacted with hydroxylamine to produce the corresponding hydroxamyl phthalide, which is subsequently subjected to a dehydration reaction to produce 5-cyanophthalide.

12 Claims, 1 Drawing Sheet

PROCESS FOR THE PREPARATION OF 5-CYANOPHTHALIDE STARTING FROM 5-CARBOXYPHTHALIDE

CROSS-REFERENCE TO RELATED APPLICATIONS

This application claims the benefit of European Application No. 05425720.9, filed Oct. 14, 2005, incorporated herein by reference in its entirety.

TECHNICAL FIELD

The present invention relates to a new process for obtaining 5-cyanophthalide, which is an intermediate used for the synthesis of citalopram and its active enantiomer S(+) citalopram, both of which are known active ingredients commonly used for treating depression.

The claimed process involves starting from 5-carboxyphthalide which, in its acyl chloride form, is reacted with hydroxylamine to give the corresponding hydroxamyl phthalide which is subsequently subjected to a dehydration reaction to produce 5-cyanophthalide.

BACKGROUND

Citalopram is a drug which has been known for some time for the treatment of depression. Because it has a chiral center, citalopram is normally produced and marketed in the form of a racemic mixture.

The S(+) enantiomer, better known as escitalopram, is responsible for almost all of the pharmacological activity of the citalopram racemate. The preparation of citalopram is described, for example, in European patent application EP1032566 while that of its enantiomer, escitalopram, is described, for example, in European patent application EP347066, both of which are incorporated herein by reference in their entirety. Both of the above-mentioned methods provide for starting from a common intermediate, 5-cyanophthalide, whose structural formula is indicated below.

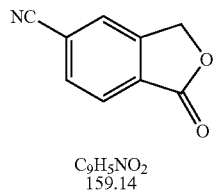

$C_9H_5NO_2$
159.14

Numerous publications describe methods for the preparation of 5-cyanophthalide. One such method was originally proposed by L. F. Levy and H. Stephen, *J. Chem. Soc.*, 867 (1931). Said method involves starting from 5-aminophthalide, which is converted into 5-cyanophthalide by means of a diazotization reaction followed by a reaction with CuCN.

Other methods have been described over the years. For example, EP1140886 describes a method for the synthesis of 5-cyanophthalide starting from 5-carboxyphthalide. The method provides for a reaction between 5-carboxyphthalide and a chlorinating agent, such as thionyl chloride. This produces the chlorocarbonyl derivative, which is then reacted with alkylamines or ammonia to give the corresponding carbamyl derivatives. When subjected to a dehydration reaction, the carbamyl derivatives give 5-cyanophthalide. The yields of 5-cyanophthalide starting from 5-carboxyphthalide reported in EP1140886 are on the order of 68%.

EP 1254129, on the other hand, provides for the synthesis of 5-cyanophthalide by reacting a thiazolyl intermediate and an oxazolidine derivative of 5-carboxyphthalide. The product is subsequently dehydrated to give cyanophthalide.

All of the methods mentioned above describe processes in which it is necessary to isolate the reaction intermediates and/or to use potentially dangerous reagents, such as ammonia or alkylamines. There remains a need in the art for methods of producing 5-cyanophthalide starting from 5-carboxyphthalide with improved yields, scalability and process safety.

BRIEF SUMMARY

The following aspects and embodiments thereof described and illustrated below are meant to be exemplary and illustrative, not limiting in scope.

In one aspect, a "one-pot process" which enables 5-cyanophthalide to be obtained directly from 5-carboxyphthalide has now surprisingly been found and forms the main subject-matter of the present invention. The claimed method provides for the transformation of 5-carboxyphthalide into 5-chlorocarbonyl phthalide. Preferably, this intermediate is not isolated and, by reaction with hydroxylamine, it is converted into 5-hydroxamyl phthalide, whose structural formula is indicated below with optimum reaction yields and a high degree of purity.

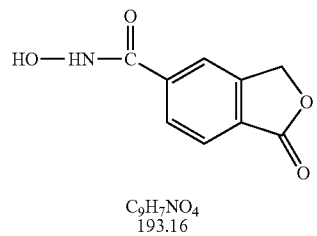

$C_9H_7NO_4$
193.16

This compound is then subjected to dehydration by means of suitable dehydrating agents, such as thionyl chloride or phosphorus oxychloride, to give 5-cyanophthalide obtained with optimum yields and a high standard of purity. The entire sequence of the process is shown in FIG. 1.

In addition to the exemplary aspects and embodiments described above, further aspects and embodiments will become apparent by reference to the drawings and by a study of the following description.

DETAILED DESCRIPTION

Figure 1:
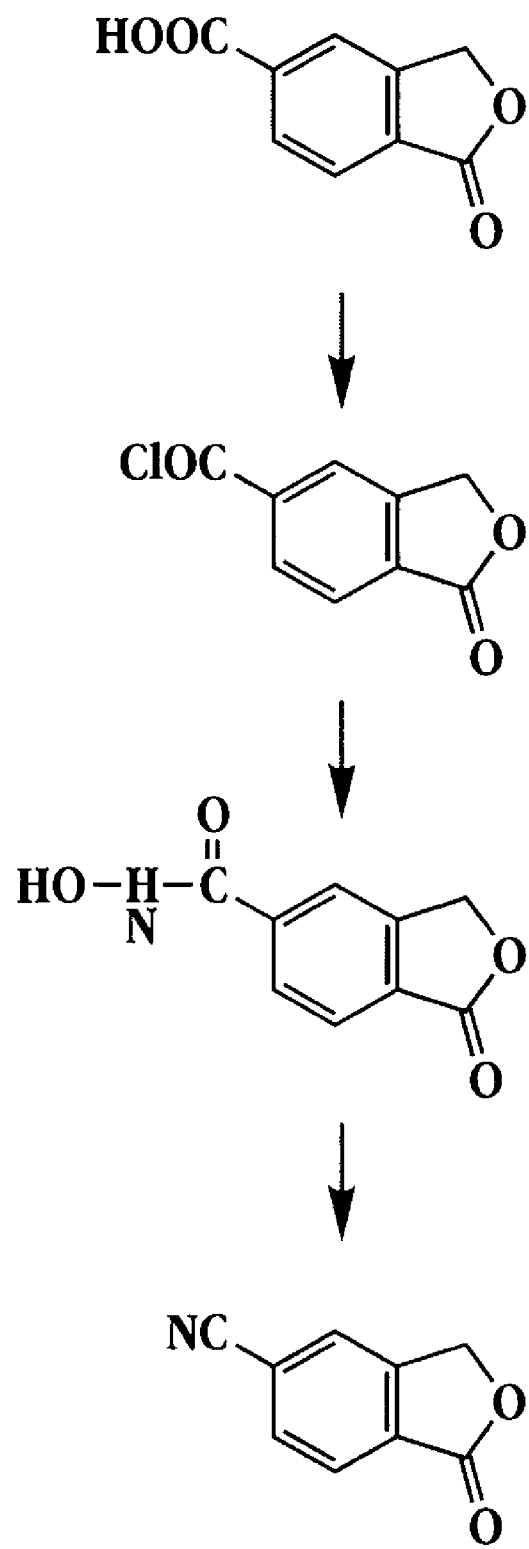
FIG. 1 shows the process starting from 5-carboxyphthalide which, in its acyl chloride form, is reacted with hydroxylamine to give the corresponding hydroxamyl phthalide which is subsequently subjected to a dehydration reaction to produce 5-cyanophthalide.

The present invention relates to a process for the production of 5-cyanophthalide comprising:
 (a) the conversion of 5-carboxyphthalide into 5-halocarbonyl phthalide;
 (b) the subsequent conversion of the 5-halocarbonyl phthalide into 5-hydroxamyl phthalide; and (c) the subsequent dehydration of the 5-hydroxamyl phthalide.

I. Method of Production

According to one aspect of the invention, 5-halocarbonyl phthalide corresponds to 5-chorocarbonyl phthalide. The latter is obtained by reacting 5-carboxyphthalide with a chlorinating agent, preferably selected from thionyl chloride, phosphorus pentachloride, sulphuryl chloride or mixtures thereof.

The above-mentioned reaction is carried out in the presence of an aprotic, polar, organic solvent, preferably at reflux temperature. This solvent is preferably selected from DMF, DMSO, or mixtures thereof, and also performs the function of catalyzing the reaction.

According to a further aspect of the invention, 5-halocarbonyl phthalide is not isolated or purified. 5-hydroxamyl phthalide is then obtained by reacting 5-halocarbonyl phthalide with hydroxylamine. This reaction is readily carried out in an aprotic organic solvent, preferably selected from THF, toluene, or mixtures thereof. The reaction temperature is preferably from 0 to +20° C., and even more preferably from +5 to +15° C.

The conversion of 5-hydroxamyl phthalide into 5-cyanophthalide is carried out in the presence of dehydrating agents, preferably selected from thionyl chloride, phosphorus oxychloride, sulphuryl chloride or mixtures thereof. According to one aspect of the invention, the dehydrating agent is used as a solvent for the reaction which is preferably carried out at the reflux temperature of the solvent.

As will be appreciated from the following Examples, which are purely illustrative and non-limiting with respect to the invention, the present process permits the production of 5-cyanophthalide starting from 5-carboxyphthalide with yields of 80%. These yields are approximately 18% higher than those reported in EP1140886. In addition, the use of hydroxylamine instead of ammonia is an improvement in terms of the scalability and safety of the process.

II. Examples

The following examples further illustrate the subject matter described herein and are in no way intended to limit the scope.

Example 1

Synthesis Of 5-Chlorocarbonyl Phthalide

The following reagents are introduced into a flask in an inert nitrogen atmosphere: 5-carboxyphthalide (50 g, 0.2806 mole), thionyl chloride (125 ml, 1.71 mole), and dimethylformamide (0.5 ml). The system is heated under reflux at 60° C. for 5 hours.

The system is returned to ambient temperature and evaporated under a vacuum to leave a residue. Toluene (3×100 ml) is introduced and a solid is obtained which is taken up with tetrahydrofuran (500 ml). A solution containing 50 g of 5-chlorocarbonyl phthalide (purity HPLC (A %) 98%) (titrated in solution, molar yield 91%) is obtained.

Example 2

Synthesis Of Cyanophthalide Starting From 5-Hydroxamyl Phthalide

Hydroxylamine HCl (8.86 g, 0.1275 mole), triethylamine (12.9 g, 0.1275 mole) and tetrahydrofuran (30 ml) are introduced into a flask. The system is brought to 10° C. A solution of 5-chlorocarbonyl phthalide (100 ml corresponding to approximately 11 g of 5-chlorocarbonyl phthalide 0.056 per mole) is added dropwise over a period of 1 hour.

The system is left under agitation for 1 hour and is then evaporated under a vacuum. A solid is observeable and 5-hydroxamyl phthalide 10 g (molar yield 92% P %=99.16%) is filtered off; 1 HNMR (DMSO-d6 400 MHz) 5.45 (2H,s), 7.87 (1Hs), 7.91 (1H,s), 7.98 (1H,s), 9.30 (1H,s), 11.52 (1H,s).

2 g of 5-hydroxamyl phthalide (0.01 mole) is introduced into a flask to which thionyl chloride (15 ml) is added. The system is heated under reflux at 80° C. to give, after 6 hours, a light yellow solution.

Toluene (20 ml) is introduced. The system is evaporated under a vacuum to leave a residue which is dissolved with toluene (20 ml). The system is heated under reflux and precipitation is awaited. Filtration is carried out to give 1.5 g of 5-cyanophthalide (molar yield 91%) (purity HPLC (A %) 99%); 1 HNMR (DMSO-d6 400 MHz) 5.45 (2H,s), 7.87 (1Hs), 7.91 (1H,s), 7.98 (1H,s).

Example 3

"One-Pot" Synthesis Of Cyanophthalide Starting From 5-Carboxyphthalide

The following reagents are introduced into a flask in an inert nitrogen atmosphere: 5-carboxyphthalide (50 g, 0.2806 mole), thionyl chloride (125 ml, 1.71 mole), and dimethylformamide (0.5 ml). The system is heated under reflux at 60° C. for 3 hours.

The system is returned to ambient temperature. The system is evaporated under a vacuum to leave a residue, and toluene (3×100 ml) is introduced. A solid is obtained which is dissolved with tetrahydrofuran (500 ml). A solution containing 50 g of 5-chlorocarbonyl phthalide (purity HPLC (A %) 98%) (titrated in solution, molar yield 91%) is obtained.

An aqueous hydroxylamine solution (18 ml, 12.5 g, 0.378 mole) is introduced into a flask. The system is brought to 10° C. A chlorocarbonyl phthalide solution (100 ml corresponding to approximately 11 g of chlorocarbonyl phthalide per 0.056 mole) is introduced (period of introduction 1 hour). The appearance of a solid is observed during the dropwise addition. The system is left under agitation overnight and then filtered.

The solid is washed with water (100 ml) and 10.5 g of 5-hydroxamyl phthalide (molar yield 92% P %=99%) is obtained; 1 HNMR (DMSO-d6 400 MHz) 5.45 (2H,s), 7.87 (1Hs), 7.91 (1H,s), 7.98 (1H,s), 9.30 (1H,s), 11.52 (1H,s).

2 g of 5-hydroxamyl phthalide (0.01 mole) is introduced into a flask to which thionyl chloride (15 ml) is added. The system is heated under reflux at 80° C. to produce, after 6 hours, a light yellow solution.

Toluene (20 ml) is introduced. The system is evaporated under a vacuum to leave a residue which is dissolved with toluene (20 ml). The system is heated under reflux and precipitation is awaited. Filtration is carried out and 1.5 g of cyanophthalide (molar yield 91%) (purity HPLC (A %) 99%) is obtained; 1 HNMR (DMSO-d6 400 MHz) 5.45 (2H,s), 7.87 (1Hs), 7.91 (1H,s), 7.98 (1H,s).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A process for the production of 5-cyanophthalide comprising: (a) converting 5-carboxyphthalide into 5-halocarbonyl phthalide by reacting 5-carboxyphthalide with thionyl chloride; (b) converting the 5-halocarbonyl phthalide into 5-phthalide-(N-hydroxycarboxamide), and; (c) dehydrating the 5-phthalide-(N-hydroxycarboxamide) with thionyl chloride.

2. A process according to claim 1, wherein step (a) comprises converting in the presence of an aprotic, polar, organic solvent.

3. A process according to claim 2, wherein step (a) comprises converting at reflux temperature.

4. A process according to claim 2, wherein the aprotic, polar, organic solvent comprises a solvent selected from the group consisting of DMF and/or DMSO.

5. A process according to claim 1, wherein the 5-halocarbonyl phthalide is not isolated or purified.

6. A process according to claim 1, wherein step (b) further comprises reacting the 5-halocarbonyl phthalide with hydroxylamine.

7. A process according to claim 1, wherein step (b) comprises converting in an aprotic organic solvent.

8. A process according to claim 7, wherein the organic solvent is selected from THF and/or toluene.

9. A process according to claim 1. wherein step (b) comprises converting at a temperature of from 0 to +20° C.

10. A process according to claim 1, wherein step (b) comprises converting at a temperature of from +5 to +15° C.

11. A process according to claim 1, wherein the dehydrating agent is used as a reaction solvent.

12. A process according to claim 11, wherein step (c) comprises dehydrating at the reflux temperature of the solvent.

* * * * *